Figure 1:
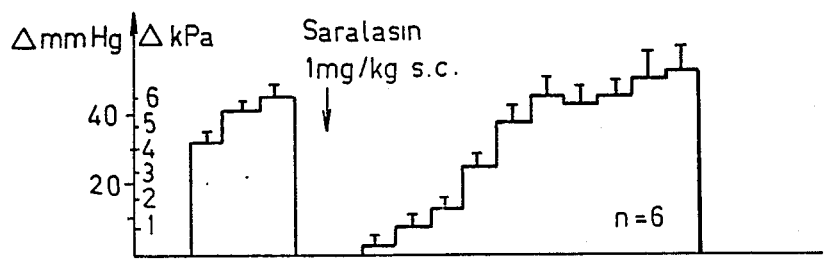
Figure 1:
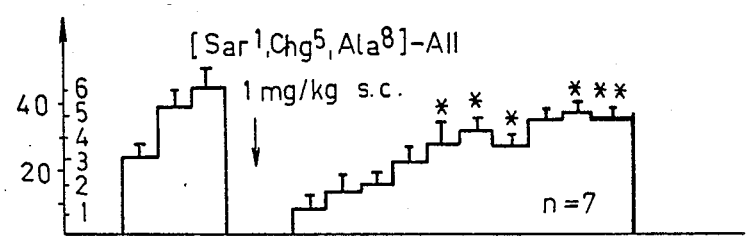
Figure 1:
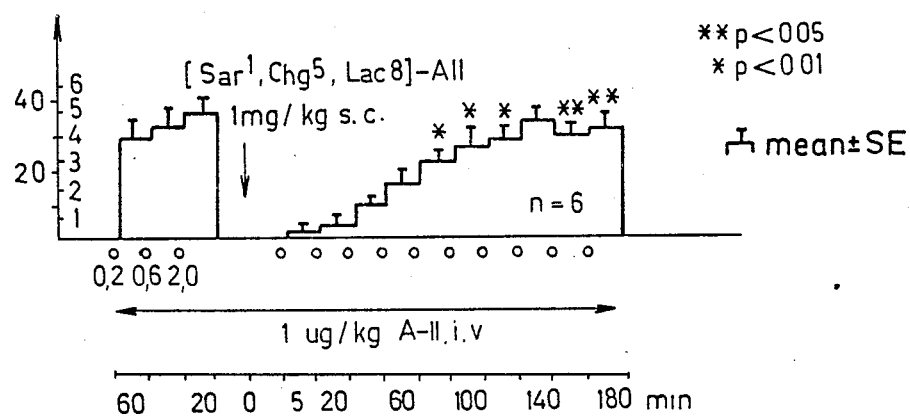

United States Patent [19]

Nyéki née Kuprina et al.

[11] Patent Number: 4,672,054
[45] Date of Patent: Jun. 9, 1987

[54] PROCESS FOR THE PREPARATION OF ANGIOTENSIN-II ANALOGUES SUBSTITUTED IN THE 1-, 5- AND 8-POSITIONS

[75] Inventors: Olga Nyéki née Kuprina; Lajos Kisfaludy; Katalin Szeberényi née Szalay; Gábor Makara; Bertalan Varga; Egon Kárpáti; László Szporny, all of Budapest, Hungary

[73] Assignee: Richter Gedeon Vegyeszeti Gyar Rt., Budapest, Hungary

[21] Appl. No.: 761,596

[22] Filed: Aug. 1, 1985

[30] Foreign Application Priority Data

Aug. 2, 1984 [HU] Hungary .............................. 2944/84

[51] Int. Cl.$^4$ ....................... A61K 37/24; C07K 7/14
[52] U.S. Cl. ...................................... 514/16; 530/316
[58] Field of Search .......................... 530/316; 514/16

[56] References Cited

U.S. PATENT DOCUMENTS

| | | | |
|---|---|---|---|
| 3,751,404 | 8/1973 | Sipos et al. | 530/316 |
| 3,915,946 | 10/1975 | Bumpus et al. | 530/316 |
| 3,915,948 | 10/1975 | Wille | 530/316 |
| 3,923,770 | 12/1975 | Bumpus et al. | 530/316 |
| 3,923,771 | 12/1975 | Bumpus et al. | 530/316 |
| 3,925,345 | 12/1975 | Bumpus et al. | 530/316 |
| 3,976,770 | 8/1976 | Bumpus et al. | 530/316 |
| 4,013,791 | 3/1977 | Wissmann et al. | 530/316 |
| 4,179,433 | 12/1979 | Kisfaludy et al. | 530/316 |
| 4,204,991 | 5/1980 | Hallinan et al. | 530/316 |
| 4,209,442 | 6/1980 | Kisfaludy et al. | 530/316 |
| 4,388,304 | 6/1983 | Nyeki et al. | 530/316 |

*Primary Examiner*—Delbert R. Phillips
*Attorney, Agent, or Firm*—Karl F. Ross; Herbert Dubno; Jonathan E. Myers

[57] ABSTRACT

The invention relates to octapeptides of the formula $$X\text{-Arg-Val-Tyr-}Y\text{-His-Pro-}W \qquad (I)$$

wherein

X is a sarcosyl, lactoyl or hydroxyacetyl radical,
Y is cyclopentylglycyl or cyclohexylglycyl, and
W is an alanine radical or lactic acid radical having angiotensine-II antagonistic activity.

6 Claims, 2 Drawing Figures

PROCESS FOR THE PREPARATION OF ANGIOTENSIN-II ANALOGUES SUBSTITUTED IN THE 1-, 5- AND 8- POSITIONS

The invention relates to new peptides of the formula

X-Arg-Val-Tyr-Y-His-Pro-W     (I)

wherein
X stands for a sarcosyl, lactoyl or hydroxyacetyl radical,
Y is cyclopentylglycyl or cyclohexylglycyl,
W is an aliphatic amino acid radical or lactic acid radical,
having angiotensin-II antagonistic activity, and to pharmaceutical compositions containing them as active ingredient.

Angiotensin-II (furtheron AII), which is liberated from angiotensin-I by the converting enzyme, exerts its hypertensive activity in the organisms according to a double mechanism. On the one hand, AII has a direct effect on the involuntary muscles, and as a result of muscle contraction increases the peripheral resistance and thereby the blood pressure. On the other hand, AII increases the aldosterone evolution in the adrenal cortex, and the increased aldosterone production, accompanied by sodium and water retention, also results in the increase of blood pressure.

AII antagonists are those structural analogues of AII, which block the AII receptors in both mechanisms, and in this manner prevent the hormone from exerting its activity.

Since the synthesis of the first effective analogues (Published Unexamined German Patent Application No. 2,127,393) numerous AII antagonists have been prepared. It turned out that in the particularly potent antagonists the phenylalanine group in the 8-position is substituted by an amino acid having an aliphatic side-chain. The activity can be increased by incorporating sarcosyl, succinyl, aminooxyacetyl, etc. groups in the 1-position and hydroxyacids in the 8-position (Published Unexamined German Patent Applications Nos. 2,758,483, 2,602,803, 2,846,200 and Hungarian Patent Specifications Nos. 177,133, 177,134 and 181,008).

These modifications resulted in active AII antagonists but up to the present there is only one AII analogue ([Sar$^1$, Val$^5$, Ala$^8$]-AII analogue, Saralasin$^R$) placed on the market for diagnostic use. The more comprehensive use of AII antagonists, in addition to their short duration of activity, is strongly limited by the fact that the hitherto synthetized analogues without exception had a temporary agonistic activity as well [Fed. Proc., 35, 2486 (1976)]. For example, [Sar$^1$, Thr(OMe)$^8$]-AII, which is a potent antagonist (U.S. Pat. No. 3,976,770) induced an initial 1.7 to 2.0 kPa (13 to 15 mmHg) increase in blood pressure in in vivo experiments [J. Med. Chem., 20, 1051 (1977)]. On the other hand, the analogues with no or little temporary agonistic effect proved to be poor antagonists. For example, [Sar$^1$, Thr$^8$]-AII has a small agonistic activity but shows no aldosterone release inhibiting effect [Eur. J. Clin. Pharm., 23, 7 (1982)]. Hence, there has so far not been synthesized any AII analogue with a significant antagonistic activity and at the same time with no or little temporary agonistic activity.

We have found that by replacing the isoleucine in the 5-position by cyclohexylglycine or cyclopentylglycine, AII inhibitors are obtained, which have a remarkable, prolonged hypotensive activity, the most potent aldosterone release inhibiting activity of the hitherto known antagonists, and a low temporary agonistic activity.

According to the invention octapeptides of the formula

X-Arg-Val-Tyr-Y-His-Pro-W     (I)

are prepared by preparing a protected octapeptide of the formula

Z-X$^1$-Arg(A)-Val-Tyr(B)-Y-His(E)-Pro-W-OG     (II)

wherein
Y and W are as defined above, and
Z is a protecting group removable by acydolysis or catalytic hydrogenation, preferably benzyloxycarbonyl or tert.-butoxycarbonyl,
A is a group suitable for the temporary protection of the guanidino group of arginine, preferably nitro group,
B is a group suitable for the temporary protection of the aromatic hydroxyl group of tyrosine, preferably benzyl or substituted benzyl,
E is a group suitable for the temporary protection of the imidazole group of histidine, preferably dinitrophenyl,
G is a group suitable for the temporary protection of the C-terminal carboxyl group, resistant to acid treatment but removable for example by catalytic hydrogenation, for example benzyl or substituted benzyl, and
X$^1$ depending on the meaning of X, either is a sarcosyl group or an aliphatic carboxylic acid radical containing an aminooxy group in the α-position,
by active ester technique, stepwise, starting from the C-terminal acid, and reacting the protected octapeptide obtained with a thiol to yield a protected octapeptide of the formula Z-X$^1$-Arg(A)-Val-Tyr(B)-Y-His-Pro-W-OG     (III)

which is then subjected to catalytic hydrogenolysis.

During this treatment, if X$^1$ is an α-aminooxy-acid radical, the corresponding octapeptide of the formula (I), in which X stands for an alphahydroxyacid is obtained in a single step, due to the splitting of the N-O bond (see Hungarian Patent Specification No. 177,133).

The octapeptides of the formula (I) are purified in a manner known per se, preferably by cellulose ion exchange chromatography. As a result, compounds are generally obtained as lyophilized powders, which can be converted into the corresponding acid addition salts or complexes. The inhibiting effect of the compounds of the formula (I) on the aldosterone production and vasoconstriction was tested in in vitro experiments.

In the latter test the inhibition of vasoconstriction induced by AII is measured on isolated rabbit aorta vessel preparate [J. Pharmacol. Exp. Ther., 108, 129 (1953)]. The results obtained are set forth in Table 1 (in pA$_2$).

The aldosterone production inhibiting activity is also shown in Table 1.

TABLE 1

| AII analogues | inhibition of aldosterone production pA$_2$ | vaso-constriction inhibition, pA$_2$ |
| --- | --- | --- |
| Sar$^1$, Chg$^5$, Ala$^8$—AII | 9.981 | 11.18 |
| Sar$^1$, Cpg$^5$, Ala$^8$—AII | 9.933 | 9.42 |
| Sar$^1$, Chg$^5$, Lac$^8$—AII | 10.390 | 11.29 |
| Sar$^1$, Cpg$^5$, Lac$^8$—AII | 9.649 | 11.09 |
| Lac$^1$, Cpg$^5$, Lac$^8$—AII | 8.392 | 8.52 |
| HOAc$^1$, CHg$^5$, Lac$^8$—AII | 8.614 | 9.53 |
| Sar$^1$, Val$^5$, Ala$^8$—AII (control)* | 9.634 | 11.10 |
| Sar$^1$, Lac$^8$—AII (control)** | 9.649 | 11.02 |
| Sar$^1$, Lac$^8$—AII—OEt (control)** | 9.27 | |
| Sar$^1$, HMV$^8$—AII (control)** | 10.589 | |
| OGly$^1$, Ile$^8$—AII (control)*** | 7.94 | |
| Sar$^1$, Ile$^8$—AII—OMe (control)**** | 8.98 | |

*Saralasin
**compound according to Hungarian Patent Specification No. 181,008
***compound according to Hungarian Patent Specification No. 177,134
****compound according to Hungarian Patent Specification No. 181,009

Though Sar$^1$, HMV$^8$-AII used as a control possesses a strong aldosterone production inhibiting activity, its pharmacological application is limited by the fact that when administered in a 10 μg/kg dose, it shows a 2.6 kPa (19.6 mmHg) initial hypertensive activity.

The results set forth in Table 1 show that certain representatives of the new analogues according to the invention show essentially the same aldosterone production inhibiting activity than the control compounds, while others are more potent.

The hypotensive activity of the new compounds was tested in vivo on awake rats, according to the modified method by Pals [Circ. Res. 29, 664 (1971)].

The results are illustrated in FIG. 1.

At first a dose—effect curve was registered for AII on rats. The peptides were administered subcutaneously, in 1 mg/kg doses. In the fifth minute after administration and repeatedly in the next three hours 1.0 μg/kg of AII was added intravenously. The statistical evaluation was performed by variancy analysis.

The results illustrated by the Figure show that of the new analogues [Sar$^1$, Chg$^5$, Ala$^8$]-AII and [Sar$^1$, Chg$^5$, Lac$^8$]-AII on awake rats have a signicantly more prolonged hypotensive activity than Saralasin used as a control.

Figure 2:
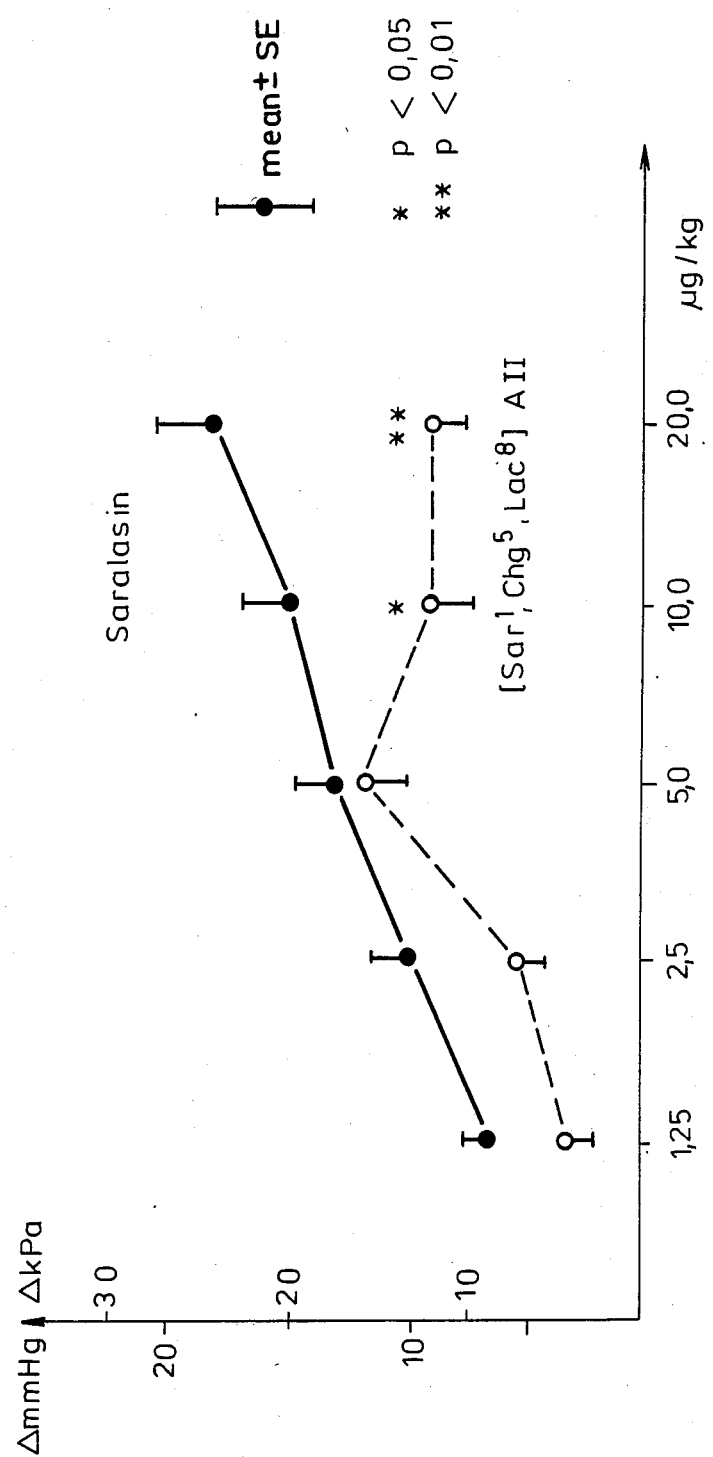

The temporary hypertensive activity of the AII analogues was tested also on awake rats. AII analogues were administered into the jugular vein in every 20 minutes. The results were evaluated by variancy analysis. The comparative results obtained on [Sar$^1$, Chg$^5$, Lac$^8$]-AII are shown on FIG. 2.

According to the data illustrated on the Figure this analogue has a significantly lower initial hypertensive activity than Salarasine used as a control substance.

The invention will now be illustrated in greater detail by the following non-limiting Examples.

The abbreviations used in the specification are symbols generally accepted in the art [J. Biol. Chem. 247, 977 (1972)]. For the abbreviation of alpha-amino-oxyacids the symbol "O" has been employed together with the symbol of the corresponding amino acid (e.g. OGly=alpha-aminooxy-acetic acid).

During the preparation of the compounds the solvent was eliminated in a Rotavapor equipment (Büchi). Melting points were determined in a Tottoli apparatus. For thin layer chromatography Kieselgel 60 F$_{254}$ layers (Merck) were used and the chromatograms were developed in the following solvent mixtures, where the ratios are indicated by volumes.

1. ethyl acetate:(pyridine:acetic acid:water = 20:6:11) = 95:5
2. ethyl acetate:(pyridine:acetic acid:water = 20:6:11) = 90:10
3. ethyl acetate:(pyridine:acetic acid:water = 20:6:11) = 80:20
4. ethyl acetate:(pyridine:acetic acid:water = 20:6:11) = 70:30
5. n-butanol:acetic acid:water = 4:1:5 (upper phase)
6. n-butanol:ethyl acetate:acetic acid:water = 1:1:1:1

The thin layer chromatograms were developed with ninhydrine, or after chlorination, with o-tolydine + potassium iodide solution.

The optical rotation was determined by a Perkin-Elmer 141 polarimeter.

The end product was purified by dissolving 0.5 g of free peptide in 4 ml of a 0.01 molar ammonium acetate solution, and pouring the solution onto a column filled with 0.5 ml of carboxymethyl cellulose (CMC 52), which has previously been balanced with the above buffer. By combining 0.01 molar and 0.5 molar ammonium acetate solutions with a gradient stirrer, gradient elution is carried out for 4 days, at a flow rate of 25 ml/hour. The eluate discharged from the column is continuously registered by an LKB Uvicord-II, whereupon on the basis of the curve obtained, the main fraction is lyophilized. Boc-Chg-OPfp and Boc-Cpg-OPfp used for the synthesis are new compounds.

Melting point: 91° to 94° C. and 98° to 99° C., respectively; $[\alpha]_D^{24} = -20.2°$ and $-31.8°$, respectively.

EXAMPLE 1

Z-Sar-Arg(NO$_2$)-Val-Tyr(Bzl)-Chg-His(Dnp)-Pro-Ala-ONB 2.0 g (8 mmoles) of Ala-ONB.HCl are dissolved in 30 ml of chloroform, and 1.12 ml of triethyl amine and 1.52 g (4 mmoles) of Boc-Pro-OPfp are added. After stirring at room temperature for 30 minutes, the solution is shaken with water and with a 10% citric acid solution. After drying and evaporation the protected dipeptide ($R_f^1 = 0.7$) is dissolved in 8 ml of a 8 n solution of hydrochloric acid in dioxane, without isolation, after 15 ml the solution is diluted with dry ether and evaporated. The free dipeptide hydrochloride ($R_f^4 = 0.65$) is dissolved in 20 ml of dimethyl formamide, the pH is adjusted to 8 with triethyl amine, and 3.52 g (6 mmoles) of Boc-His(Dnp)-OPfp are added. After stirring for 30 minutes the solvent is eliminated, the oily residue is dissolved in 50 ml of ethyl acetate, and 0.88 ml of N,N-dimethylamino-ethylamine are added. After 15 minutes the solution is shaken with a 10% citric acid solution, 1 n hydrochloric acid, water and 5% sodium bicarbonate solution. After drying and evaporation the oily residue is solidified with 30 ml of ether, the precipitate is filtered off and washed with ether. 2.5 g (88%) of the protected tripeptide are obtained, $R_f^2 = 0.60$.

1.0 g (1.42 mmoles) of Boc-His(Dnp)-Pro-Ala-ONB obtained are dissolved in 6 ml of a 8 n solution of hydrochloric acid in dioxane, whereupon after 15 minutes the free tripeptide hydrochloride ($R_f^3 = 0.30$) is precipitated with dry ether, filtered and washed with ether. It is immediately dissolved in 10 ml of dimethyl formamide, the pH is adjusted to 8 with triethyl amine, and 0.86 g of Boc-Chg-OPfp are added. After 30 minutes the reaction mixture is evaporated, the residue is dissolved in 30 ml of ethyl acetate and it is shaken with a 10% aqueous citric acid solution, water and subsequently a 5% sodium bicarbonate solution. After drying and evaporation the protected tetrapeptide ($R_f^2 = 0.8$) is solidified with 50 ml of n-hexane, filtered and washed with n-hexane. Thereafter, it is dissolved in 6 ml of a 8 n solution of hydrochloric acid in dioxane, and after 15 minutes the free tetrapeptide hydrochloride ($R_f^3=0.20$) is precipitated with dry ether, filtered and washed with ether. The product is immediately dissolved in 10 ml of dimethyl formamide, the pH is adjusted to 8 with triethyl amine, and 0.8 g (1.5 mmoles) of Boc-Tyr(Bzl)-OPfp are added. After 30 minutes the solvent is replaced by ethyl acetate, 0.11 ml of dimethylaminoethyl amine are added, and after 15 minutes the mixture is shaken with a 1 n hydrochloric acid solution, water and subsequently a 5% sodium bicarbonate solution. After drying and evaporation the protected pentapeptide ($R_f^1=0.35$) is solidified with 30 ml of ether, filtered and washed with ether. It is then dissolved in 10 ml of a 8 n solution of hydrochloric acid in dioxane, after 10 minutes the free pentapeptide hydrochloride ($R_f^3=0.35$) is precipitated with dry ether, filtered and washed with ether. It is immediately dissolved in 15 ml of dimethyl formamide, the pH is adjusted to 8 with triethyl amine, and 0.75 g (2 mmoles) of Boc-Val-OPfp are added. After stirring for 30 minutes the solvent is exchanged for chloroform, and it is shaken with a 10% citric acid solution, 1 n hydrochloric acid and water. After drying and evaporation the protected hexapeptide ($R_f^1=0.37$) is solidified, filtered and washed with ether. Thereafter, the product is dissolved in 20 ml of a 8 n solution of hydrochloric acid in dioxane, and after 15 minutes the free hexapeptide hydrochloride ($R_g^4=0.45$) is precipitated with dry ether, filtered and washed with ether. It is immediately dissolved in 15 ml of dimethyl formamide, the pH is adjusted to 8 with triethyl amine, and 0.98 g (2.0 mmoles) of Boc-Arg(NO₂)-OPfp are added. After stirring for one hour, the solution is diluted with 45 ml of chloroform, and shaken with a 10% citric acid solution, 1 n hydrochloric acid and subsequently with water. The residue obtained after drying and evaporation is solidified with ethanol, and filtered ($R_f^2=0.30$). The protected heptapeptide is dissolved in 20 ml of a 8 n solution of hydrochloric acid in dioxane, and after 20 minutes the free heptapeptide hydrochloride ($R_f^3=0.21$) is precipitated by adding dry ether, filtered, washed and immediately dissolved in 15 ml of dimethyl formamide. The pH of the solution is adjusted to 8 with triethyl amine, and there are added 0.59 g (1.5 mmoles) of Z-Sar-OPfp. After one hour, the reaction mixture is evaporated, and the oily residue is solidified with 15 ml of ethanol, filtered, and washed with ethanol and then with ether. 1.5 g (70%, related to Bos-His(Dnp)-Pro-Ala-ONB) of the title compound are obtained. Melting point: 194° C. (decomposition); $R_f^2=0.4$, $R_f^3=0.80$.

EXAMPLE 2

H-His(Dnp)-Pro-Lac-OBzl.HCl 7.3 g (30 mmoles) of lactic acid zinc salt are suspended in 40 ml of dimethyl formamide, and to the suspension 4.2 ml (30 mmoles) of triethyl amine and 0.36 g (30 mmoles) of Boc-Pro-OSu are added. After stirring for 24 hours at room temperature the solution becomes clear. Thereafter, dimethyl formamide is eliminated under reduced pressure, the residue is dissolved in 150 ml of ethyl acetate, and it is shaken with 1 n hydrochloric acid and subsequently water. After drying and evaporation Boc-Pro-Lac-OH is solidified with 50 ml of hexane and filtered. The crude product is recrystallized from a 1:1 mixture of ether and hexane (40 ml) to yield 6.6 g (77%) of the title compound. Melting point: 108° to 110° C., $[\alpha]_D^{24}=-88.2°$ (c=2, ethanol), $R_f^5=0.30$.

2.87 g (10 mmoles) of Boc-Pro-Lac-OH obtained are dissolved in 20 ml of ethyl acetate, whereupon 1.7 ml (12 mmoles) of triethyl amine and 1.42 ml (12 mmoles) of benzyl bromide are added. The solution is refluxed for 8 hours, and then it is diluted with 20 ml of ethyl acetate and shaken with water, 1 n hydrochloric acid and a 5% sodium bicarbonate solution. After drying and evaporation Boc-Pro-Lac-OBZl is obtained as an oily product. Yield: 3.05 g (81%), $R_f^1=0.67$, $[\alpha]_D^{24}=-90.0°$ (c=2, ethanol).

2.65 g (7.0 mmoles) of Boc-Pro-Lac-OBzl are dissolved in 10 ml of a 8 n solution of hydrochloric acid in dioxane. After 15 minutes the solution is diluted with dry ether and evaporated. H-Pro-Lac-OBzl hydrochloride ($R_f^4=0.2$) obtained is dissolved in 15 ml of dimethyl formamide, the pH of the solution is adjusted to 8 with triethyl amine, and 3.5 g (6 mmoles) of Boc-His(Dnp)-OPfp are added. After stirring for one hour, dimethyl formamide is evaporated, the residue is dissolved in 60 ml of ethyl acetate and shaken with a 1 n hydrochloric acid solution, water and subsequently a 5% sodium bicarbonate solution. After drying and evaporation an oily residue is obtained, which is dissolved in 15 ml of a 8 n solution of hydrochloric acid in dioxane, and after 15 minutes the free tripeptide hydrochloride ($R_f^3=0.10$) is precipitated, filtered and washed with ether. Yield: 2.8 g (78%).

The peptide chain is built up further as described in Example 1. Further AII analogues prepared in an analogeous manner are shown in Table 2.

TABLE 2

| Physical constants of protected octapeptides | | | | |
|---|---|---|---|---|
| Peptide | Yield % | Mp. °C. | $R_f^3$ | $[\alpha]_D^{24}$ c = 1, DMF |
| Z—Sar—Arg(NO₂)—Val—Tyr(Bzl)—Chg—His(Dnp)—Pro—Ala—ONB | 58* | 213(b) | 0.8 | |
| Z—Sar—Arg(NO₂)—Val—Tyr(Bzl)—Cpg—His(Dnp)—Pro—Ala—ONB | 50* | 178-181 | 0.77 | −21.4 |
| Z—Sar—Arg(NO₂)—Val—Tyr(Bzl)—Chg—His(Dnp)—Pro—Lac—OBzl | 54** | 217(b) | 0.63 | −35.9 |
| Z—Sar—Arg(NO₂)—Val—Tyr(Bzl)—Cpg—His(Dnp)—Pro—Lac—OBzl | 61** | 192-199 | 0.60 | −32.7 |
| Z—OAla—Arg(NO₂)—Val—Tyr(Bzl)—Cpg—His(Dnp)—Pro—Lac—OBzl | 58** | 180-184 | 0.76 | −44.3 |
| Z—OGly—Arg(NO₂)—Val—Tyr(Bzl)—Chg—His(Dnp)—Pro—Lac—OBzl | 61** | 180-183 | 0.65 | −26.6 |

*The yield is calculated for BOC—Pro—OPfp.
**The yield is calculated for BOC—His(Dnp)—Pro—Lac—OBzl.

EXAMPLE 3

Elimination of the protecting groups 1.5 g (1 mmoles) of Z-Sar-Arg(NO$_2$)-Val-Tyr(Bzl)-CHg-His(Dnp)-Pro-Ala-ONB are dissolved in 5 ml dimethyl formamide, 1.9 ml (25 mmoles) of 2-mercaptoethanol are added, and after stirring for one hour, the product is precipitated with dry ether, filtered and washed with ethanol. 1.23 g (91%) of Z-Sar-Arg(NO$_2$)-Val-Tyr(Bzl)-Chg-His-Pro-Ala-ONB are obtained. $R_f^2 = 0.20$, $R_f^3 = 0.40$. The material in a 5:1:1 (by volume) mixture of methanol, acetic acid and water, 0.6 g of a 10% palladium-on-charcoal catalyst are added, and hydrogen gas is bubbled through the mixture with stirring for 25 hours. The termination of the reaction is controlled by thin layer chromatography. The catalyst is then filtered off, and the solution is evaporated to dryness. To the residue a 9:1 mixture (by volume) of ethanol and water is added, it is evaporated and the residue is solidified with ethanol, filtered and washed with ethanol. 0.7 g (74%) of Sar$^1$, Chg$^5$, Ala$^8$-AII are obtained. The product is purified as described above. $R_f^5 = 0.10$, $R_f^6 = 0.27$, $[\alpha]_D^{24} = -84.5°$ (c=0.3, 1 m AcOH).

Amino acid analysis: Pro1(1), Ala 1.15 (1), Val 0.95, (1), His 0.85(1), Tyr 0.86 (1).

Further free octapeptides prepared in an analogous manner are disclosed in Table 3.

TABLE 3

Characteristic data of free octapeptides

| Peptides | Yield* % | $R_f$ 5 | $R_f$ 6 | $[ ]_D^{24}$** | Amino acid analysis |
|---|---|---|---|---|---|
| Sar$^1$,CHg$^5$,Ala$^8$—AII | 74 | 0.10 | 0.27 | −84.5° | Arg 1, Pro 1, His 0.85, Ala 1.15 Val 0.95, Tyr 0.86, Chg 1.02 |
| Sar$^1$,Cpg$^5$,Ala$^8$—AII | 69 | 0.10 | 0.13 | −92.7° | Arg 0.95, Pro 1.06, His 0.92 Ala 1.03, Val 1.03, Tyr 0.80 Cpg 0.97 |
| Sar$^1$,Chg$^5$,Lac$^8$—AII | 72 | 0.16 | 0.20 | −87.5° | Arg 0.95, Pro 1.01, His 0.92, Val 1.04, Tyr 0.49, Chg 1.09 |
| Sar$^1$,Cpg$^5$,Lac$^8$—AII | 66 | 0.15 | 0.16 | −94.6° | Arg 0.95, Pro 0.93, His 0.98, Val 1.1, Tyr 0.58, Cpg 1.02 |
| Lac$^1$,Cpg$^5$,Lac$^8$—AII | 78 | 0.08 | 0.35 | −100.7° | Arg 0.97, Pro 1.05, His 0.97, Val 1.03, Tyr 0.62, Cpg 1.05 |
| HOAc$^1$,CHg$^5$,Lac$^8$—AII | 55 | 0.20 | 0.38 | −106.4° | Arg 0.98, Pro 1.08, His 0.90, Val 1.05, Tyr 0.67, Chg 1.05 |

*related to protected octapeptide
**c = 0.2, 1 m AcOH

We claim:

1. A compound of the Formula (I)

X-Arg-Val-Tyr-Y-His-Pro-W wherein
    X is a sarcosyl, lactyl, or hydroxyacetyl radical;
    Y is cyclopentylglycyl or cyclohexylglycyl; and
    W is an alanine radical or a lactic acid radical.

2. The compound of the Formula (I) defined in claim 1 selected from the group consisting of:
    (a) sarcosyl$^1$, cyclohexylglycyl$^5$, alanine$^8$-angiotensin II;
    (b) sarcosyl$^1$, cyclopentylglycyl$^5$, alanine$^8$-angiotensin II;
    (c) sarcosyl$^1$, cyclohexylglycyl$^5$, alanine$^8$-angiotensin II;
    (d) sarcosyl$^1$, cyclopentylglycyl$^5$, lactic acid$^8$-angiotensin II;
    (e) lactyl$^1$, cyclopentylglycyl$^5$, lactic acid$^8$-angiotensin II; and
    (f) hydroxyacetyl$^1$, cyclohexylglycyl$^5$, lactic acid$^8$-angiotensin II.

3. An antihypertensive composition which comprises a therapeutically effective amount of the compound of the Formula (I) as defined in claim 1 together with a pharmaceutically acceptable inert carrier.

4. A method of reducing high blood pressure in a mammalian subject which comprises the step of administering to said mammalian subject a therapeutically effective amount of the compound of the Formula (I) as defined in claim 1.

5. A compound of the Formula (II)

X$^1$-Arg(A)-Val-Tyr(B)-Y-His(E)-Pro-W-OG wherein
    Y is cyclopentylglycyl or cyclohexylglycyl;
    W is alanyl or lactyl;
    A is a group suitable for the temporary protection of the guanidino group of arginine;
    B is a group suitable for the temporary protection of the aromatic hydroxy group of tyrosine;
    E is a group suitable for the temporary protection of the imidazole group of histidine;
    G is a group suitable for the temporary protection of the C-terminal carboxyl group, resistant to acid treatment but removable by catalytic hydrogenation;
    X$^1$ is either Z-sarcosyl or is lactyl or hydroxyacetyl each having its alpha-hydroxy group blocked by Z—NH—; and
    Z is a protecting group removable by acidiolysis or catalytic hydrogenation.

6. A compound of the Formula (III)

X$^1$-Arg(A)-Val-Tyr(B)-Y-His-Pro-W-OG wherein
    Y is cyclopentylglycyl or cyclohexylglycyl;
    W is alanyl or lactyl;
    A is a group suitable for the temporary protection of the guanidino group of arginine;
    B is a group suitable for the temporary protection of the aromatic hydroxy group of tyrosine;
    G is a group suitable for the temporary protection of the C-terminal carboxyl group, resistant to acid treatment but removable by catalytic hydrogenation;
    X$^1$ is either Z-sarcosyl or is lactyl or hydroxyacetyl each having its alpha-hydroxy group blocked by Z—NH—; and
    Z is a protecting group removable by acidiolysis or catalytic hydrogenation.

* * * * *